US010029078B2

(12) United States Patent
Murata (10) Patent No.: US 10,029,078 B2
(45) Date of Patent: Jul. 24, 2018

(54) PANCREAS PERFUSION APPARATUS, METHOD FOR CONTROLLING SAME, AND METHOD FOR PANCREAS PERFUSION

(71) Applicant: KOSEI ADVANCE CO., LTD., Kawagoe-shi (JP)

(72) Inventor: Satoru Murata, Tokyo (JP)

(73) Assignee: KOSEI ADVANCE CO., LTD., Saitama (JP)

( * ) Notice: Subject to any disclaimer, the term of this patent is extended or adjusted under 35 U.S.C. 154(b) by 250 days.

(21) Appl. No.: 15/026,835

(22) PCT Filed: Oct. 1, 2014

(86) PCT No.: PCT/JP2014/076271
§ 371 (c)(1),
(2) Date: Apr. 1, 2016

(87) PCT Pub. No.: WO2015/050154
PCT Pub. Date: Apr. 9, 2015

(65) Prior Publication Data
US 2016/0235950 A1 Aug. 18, 2016

(30) Foreign Application Priority Data
Oct. 2, 2013 (JP) .................................. 2013-207612

(51) Int. Cl.
*A61M 37/00* (2006.01)
*A61M 25/10* (2013.01)
(Continued)

(52) U.S. Cl.
CPC ...... *A61M 25/1011* (2013.01); *A61M 1/3613* (2014.02); *A61M 1/3621* (2013.01);
(Continued)

(58) Field of Classification Search
CPC ............ A61M 25/1011; A61M 1/3613; A61M 1/3659; A61M 1/3621; A61M 1/34;
(Continued)

(56) References Cited

U.S. PATENT DOCUMENTS

2009/0088676 A1* 4/2009 Murata ............... A61M 1/3621
604/6.16
2011/0295114 A1 12/2011 Agah et al.

FOREIGN PATENT DOCUMENTS

JP 2009-034462 A 12/2009

OTHER PUBLICATIONS

International search report of PCT/JP2014/076271 dated Dec. 16, 2014.
(Continued)

*Primary Examiner* — Philip R Wiest
(74) *Attorney, Agent, or Firm* — Typha IP LLC (57) ABSTRACT

Provided are a pancreas perfusion apparatus capable of administering a drug only to the pancreas and strictly suppressing a leakage of the drug outside the pancreas and a method for controlling the same. The apparatus includes: a first vein occlusion section occluding a vein through which a venous blood from the pancreas flows; a second vein occlusion section occluding a vein into which a venous blood from collateral pathways outside the pancreas flows; an artery occlusion section occluding sites where an artery that nourishes the pancreas is connected to arteries that nourish other tissues; a drug administration section recovering a liquid upstream of the first vein occlusion section and supplying the recovered liquid to the artery; a systemic circulation section recovering a liquid upstream of the second vein occlusion section and feeding the recovered liquid into a systemic circulation; and a control device controlling the systemic circulation pump.

15 Claims, 4 Drawing Sheets

(51) Int. Cl.
  *A61M 1/36* (2006.01)
  *A61M 5/142* (2006.01)
  *A61M 31/00* (2006.01)
  *A61M 1/34* (2006.01)
(52) U.S. Cl.
  CPC .......... *A61M 1/3659* (2014.02); *A61M 5/142* (2013.01); *A61M 1/34* (2013.01); *A61M 31/00* (2013.01); *A61M 2025/105* (2013.01); *A61M 2025/1052* (2013.01); *A61M 2025/1097* (2013.01); *A61M 2205/3334* (2013.01)
(58) Field of Classification Search
  CPC .................. A61M 5/142; A61M 31/00; A61M 2025/105; A61M 2025/1052; A61M 2025/1097; A61M 2205/3334
  See application file for complete search history.

(56) References Cited

OTHER PUBLICATIONS

Written Opinion of the International Preliminary Report on Patentability of PCT/JP2014/076271, dated Dec. 16, 2014.

Spano et al., Efficacy of gemcitabine plus axitinib compared with gemcitabine alone in patients with advanced pancreatic cancer: an open-label randomised phase II study, Lancet, Jun. 21, 2008, pp. 2101-2108, vol. 371, Published Online.

Bria et al., Gemcitabine based combinations for inoperable pancreatic cancer: have we made real progression? A meta analysis of 20 phase 3 trials, American Cancer society, Jun. 18, 2007, pp. 525-533, vol. 110, Published Online.

Colucci et al., Randomized Phase III Trial of Gemcitabine Plus Cisplatin Compared With Single-Agent Gemcitabine as First-Line Treatment of Patients With Advanced Pancreatic Cancer:The GIP-1 Study, 2010 by American Society of Clinical Oncology, Apr. 1, 2010, pp. 1645-1651, vol. 28, Published Online.

Philip et al., Phase III Study Comparing Gemcitabine Plus Cetuximab Versus Gemcitabine in Patients With Advanced Pancreatic Adenocarcinoma: Southwest Oncology Group-Directed Intergroup Trial S0205, 2010 by American Society of Clinical Oncology, Aug. 1, 2010, pp. 3605-3610, vol. 28, Published Online.

Jemal et al., Cancer statistics, 2008, A Cancer Journal for Clinicians, Mar./Apr. 2008, pp. 71-96, vol. 58, Published Online.

Tempero et al., Pancreatic Adenocarcinoma, NCCN (National Comprehensive Cancer Network) Clinical Practice Guideline in Oncology, National Comprehensive Cancer Network, Nov. 2007, pp. 998-1033, vol. 5, Published Online.

Burris et al., Improvements in survival and clinical benefit with gemcitabine as first-line therapy for patients with advanced pancreas cancer: a randomized trial, Journal of Clinical Oncology, Jun. 1, 1997, pp. 2403-2413, vol. 15, No. 6.

Homma et al., A novel arterial infusion chemotherapy for the treatment of patients with advanced pancreatic carcinoma after vascular supply distribution via superselective embolization, American Cancer Society, Jul. 15, 2000, pp. 303-313, vol. 89, No. 2.

Takamori et al., Perioperative intra-arterial and systemic chemotherapy for pancreatic cancer, Annals of Surgical oncology, Nov. 3, 2010, pp. 1110-1115, vol. 18, Published Online.

Ikeda et al., Evaluation of the efficacy of combined continuous arterial infusion and systemic chemotherapy for the treatment of advanced pancreatic carcinoma, Cardio Vascular and Interventional Radiology, Feb. 13, 2016, pp. 362-370, vol. 29, Published Online.

Nasu et al., Suicide gene therapy with adenoviral delivery of HSV-tK gene for patients with local recurrence of prostate cancer after hormonal therapy, The American Society of Gene Therapy, Feb. 27, 2007, pp. 834-840, vol. 15, No. 4, Published Online.

Fujiwara et al., Multicenter phase I study of repeated intratumoral delivery of adenoviral p53 in patients with advanced non-small-cell lung cancer, American Society of Clinical Oncology, Apr. 10, 2006, pp. 1689-1699, vol. 24, No. 11.

Shimada et al., Phase I/II adenoviral p53 gene therapy for chemoradiation resistant advanced esophageal squamous cell carcinoma, Japanese Cancer Association, Jun. 2006, pp. 554-561, vol. 97, No. 6.

* cited by examiner

PANCREAS PERFUSION APPARATUS, METHOD FOR CONTROLLING SAME, AND METHOD FOR PANCREAS PERFUSION

CROSS REFERENCE TO RELATED APPLICATION

This application is entering into national phase of PCT Application No. PCT/JP2014/076271, filed on Oct. 1, 2014, which claims priority of Japanese Patent Application JP2013-207612, filed on Oct. 2, 2013, which is incorporated herein by reference in its entirety.

TECHNICAL FIELD

The present invention relates to a medical treatment apparatus used in a percutaneous isolated pancreas perfusion therapy and a method for controlling the same, specifically a pancreas perfusion apparatus used for treating a lesion inside of the pancreas by perfusing the pancreas of a patient with a drug, a method for controlling the same, and a method for pancreas perfusion.

BACKGROUND ART

The pancreas is a long and slender organ, approximately 20 cm long, which lies behind the stomach. The pancreas has functions in producing pancreatic juice that assists digestion of food (external secretion) and in producing a hormone required for regulating blood sugar levels, such as insulin and glucagon (internal secretion).

Examples of pancreatic diseases include diabetes, pancreatitis, and pancreatic cancer.

Among them, pancreatic cancer does not show characteristic symptoms in an early stage and advances quickly, thus detection of pancreatic cancer tends to be delayed and it is often detected as advanced cancer. Pancreatic cancer is one of the most lethal human cancers, with 1-year and 5-year survival rates below 25% and 5%, respectively (Non Patent Literatures 1 to 5). Conventional treatment approaches, including surgery, radiation, chemotherapy, and their combinations have had little impact on the course of this aggressive neoplasm.

Although gemcitabine has been widely used in recent years as standard systemic chemotherapy for patients with unresectable pancreatic cancer (Non Patent Literature 6), the response rate is only approximately 10% and the median survival time is approximately 6 months (Non Patent Literature 7). Trials comparing gemcitabine plus various cytotoxic and/or molecular targeted agents with gemcitabine alone have shown no improvement in response or survival (Non Patent Literatures 2 to 4). The very poor prognosis of patients with advanced pancreatic cancer and the absence of efficient new drugs suggest the need for innovative modalities that may improve clinical response to available chemotherapies.

Regional chemotherapy techniques, including arterial infusion, chemoembolization, and perfusion, have been used to treat patients with advanced pancreatic cancer. More recently, arterial infusion chemotherapy has shown promise in patients with non-resectable pancreatic cancer (Non Patent Literatures 8 and 9). The pharmacological rationale for regional drug delivery is to increase drug concentrations at tumor sites and limit systemic drug exposure and its sequelae (Non Patent Literature 10). Since these anticancer drugs administered by arterial infusion ultimately enter the systemic circulation, the dose of the anticancer drugs must be strictly limited.

As such, there is currently no known local therapy in which a drug administered to the pancreas does not leak outside the pancreas. That is, in the present circumstances, a drug leaks outside the pancreas more or less even in a local therapy, thus causing a such dilemma that when a drug having high therapeutic effects for a lesion is used, side effects are caused by the systemic circulation, and conversely, when a drug having low therapeutic effects for a lesion is used in order to suppress side effects caused by the systemic circulation, the therapeutic effects for a lesion is reduced.

On the other hand, as a therapeutic method of congenital genetic diseases, cancers, peripheral vascular diseases, ischemic heart diseases, neurodegenerative diseases, viral infectious diseases, and the like, studies of clinical tests and the like involving a gene therapy have been recently conducted in various countries such as the United States of America.

A gene therapy is defined that a gene or a cell in which a gene is transferred is administered in a human body for the purpose of treating diseases (Japanese Guideline for Gene Therapy Clinical Research) and expected to be an effective therapeutic method not only for inherited diseases, but also for intractable diseases such as life-style related diseases and cancers.

As a gene therapy, clinical studies and the like of an oncogene therapy, in which a vector having a transgene integrated is directly injected into tumors, have been conducted.

For example, it is reported that as a result of directly injecting an adenovirus vector having HSV-tk integrated into prostate cancer and then continuously performing intravenous administration of ganciclovir for two weeks, a reduction of PSA (prostate specific antigen) as a marker of prostate cancer was observed without having a particularly severe adverse event in 6 out of 8 cases (Non Patent Literature 11). It is also reported that, in clinical tests where an adenovirus vector having the p53 gene integrated was used for targeting non-small-cell lung cancer and esophagus squamous epithelium carcinoma, both having a mutation in p53, the normal p53 was expressed in the tumors and anti-tumor effects were observed (Non Patent Literatures 12 and 13).

As seen in the clinical studies of prostate cancer in Non Patent Literature 11, a gene therapy has been producing good results to some extent for cancer in organs in which a drug is easily injected. However, for example, for organs located in the abdomen such as the pancreas, only known method of supplying a drug is a method involving systemic exposure of the drug, such as arterial infusion therapy, thus a gene therapeutic drug cannot be supplied in a concentrated manner and good results are not obtained.

Further, in a gene therapeutic method, a vector is used for increasing a transfer efficiency of a gene into a target cell. Among the vectors studied so far, the ones having a high gene transfer efficiency tend to have high side effects on normal cells. In order to realize a gene therapy for pancreatic cancer, a method, in which a vector having side effects does not leak outside the pancreas, needs to be established. However, at the present stage, there is no known local therapy in which a leakage of a drug is prevented strictly enough to allow a gene therapy.

Furthermore, a gene therapeutic drug is very expensive compared to a conventional drug such as an anticancer drug, thus it also needs to restrain an amount of the drug used in a single clinical test for reducing costs per clinical test.

CITATION LIST

Non Patent Literature

NON PATENT LITERATURE 1: Spano J P, Chodkiewicz C, Maurel J, et al. Efficacy of gemcitabine plus axitinib compared with gemcitabine alone in patients with advanced pancreatic cancer: an open-label randomised phase II study. Lancet 2008; 371: 2101-08.

NON PATENT LITERATURE 2: Bria E, Milella M, Gelibter A, et al. Gemcitabine based combinations for inoperable pancreatic cancer: have we made real progression? A meta analysis of 20 phase 3 trials. Cancer 2007; 110:525-533.

NON PATENT LITERATURE 3: Colucci G, Labianca R, Di Costanzo F, et al. Randomized phase III trial of gemcitabine plus cisplatin compared with single-agent gemcitabine as firstline treatment of patients with advanced pancreatic cancer: the GIP-1 study. J Clin Oncol 2010; 28: 1645-1651.

NON PATENT LITERATURE 4: Philip P A, Benedetti J. Corless C L, et al. Phase III study comparing gemcitabine plus cetuximab versus gemcitabine in patients with advanced pancreatic adenocarcinoma: Southwest Oncology Group-directed intergroup trial S0205. J Clin Oncol 2010; 28: 3605-3610.

NON PATENT LITERATURE 5: Jemal A, Siegel R, Ward E, et al. Cancerstatistics. 2008. CA Cancer J Clin 2008; 58: 71-96.

NON PATENT LITERATURE 6: NCCN (National Comprehensive Cancer Network) Clinical Practice Guideline in Oncology, Pancreatic Adenocarcinoma Version 1. 2008. http://www.nccn.org/professionals/

NON PATENT LITERATURE 7: Burris H A III, Moore M J, Andersen J, et al. Improvements in survival and clinical benefit with gemcitabine as first-line therapy for patients with advanced pancreatic cancer: a randomized trial. J Clin Oncol 1997; 15: 2403-2413.

NON PATENT LITERATURE 8: Homma H, Doi T, Mezawa S, et al. A novel arterial infusion chemotherapy for the treatment of patients with advanced pancreatic carcinoma after vascular supply distribution via superselective embolization. Cancer 2000; 89: 303-313.

NON PATENT LITERATURE 9: Takamori H, Kanemitsu K, Hirota M, et al. Perioperative intra-arterial and systemic chemotherapy for pancreatic cancer. Ann Surg Oncol 2011; 18: 1110-1115.

NON PATENT LITERATURE 10: Ikeda O, Kusunoki S, Takamori H, et al. Evaluation of the efficacy of combined continuous arterial infusion and systemic chemotherapy for the treatment of advanced pancreatic carcinoma. Cardiovasc Intervent Radiol 2006; 29: 362-370.

NON PATENT LITERATURE 11: Nasu Y, Saika T. Ebara S, Kusaka N. Kaku H, Abarzua F, Manabe D, Thompson T C, Kumon H. Suicide gene therapy with adenoviral delivery of HSV-tK gene for patients with local recurrence of prostate cancer after hormonal therapy. Mol Ther. 15(4): 834-840 (2007).

NON PATENT LITERATURE 12: Fujiwara T, Tanaka N, Kanazawa S, Ohtani S, Saijo Y, Nukiwa T. Yoshimura K, Sato T, Eto Y. Chada S. Nakamura H, Kato H. Multicenter phase I study of repeated intratumoral delivery of adenoviral p53 in patients with advanced non-small-cell lung cancer. J Clin Oncol. 24(11): 1689-1699 (2006).

NON PATENT LITERATURE 13: Shimada H. Matsubara H, Shiratori T. Shimizu T, Miyazaki S, Okazumi S, Nabeya Y, Shuto K, Hayashi H, Tanizawa T, Nakatani Y, Nakasa H, Kitada M, Ochiai T Phase I/II adenoviral p53 gene therapy for chemoradiation resistant advanced esophageal squamous cell carcinoma. Cancer Sci, 97(6): 554-561 (2006).

SUMMARY OF INVENTION

Technical Problem

The present invention has been made in view of the above-mentioned problems and it is an object of the present invention to provide a pancreas perfusion apparatus capable of administering a drug only to the pancreas and strictly suppressing a leakage of the drug outside the pancreas, a method for controlling the same, and a method for pancreas perfusion.

It is another object of the present invention to provide a pancreas perfusion apparatus, which makes it possible to use a drug having side effects by strictly suppressing a leakage of the drug outside the pancreas, a method for controlling the same, and a method for pancreas perfusion.

It is yet another object of the present invention to provide a pancreas perfusion apparatus, which makes it possible to apply a gene therapy to pancreatic diseases, a method for controlling the same, and a method for pancreas perfusion.

Solution to Problem

The inventors of the present invention has found, as a result of their earnest studies on a pancreas perfusion apparatus performing percutaneous isolated pancreas perfusion, that a drug administered to the pancreas can be strictly prevented from leaking outside the pancreas by providing, in addition to a drug administration section for administering a drug to the pancreas, a systemic circulation section for recovering a liquid from a second vein into which a venous blood from collateral pathways outside the pancreas flows and feeding the liquid into a systemic circulation, the second vein being located upstream of a first main vein through which a venous blood from the pancreas flows, and also by controlling a systemic circulation pump so as to recover the liquid at a predetermined flow rate by a control device. Thus, the inventors have completed the present invention.

That is, according to the pancreas perfusion apparatus of the present invention, the above-mentioned problems can be solved by the pancreas perfusion apparatus for administering a drug topically to the pancreas by percutaneous isolated pancreas perfusion, including: a first vein occlusion section which occludes a first main vein through which a venous blood from the pancreas flows; a second vein occlusion section which occludes a second vein into which a venous blood from collateral pathways outside the pancreas flows, the second vein being located upstream of the first main vein; an artery occlusion section which occludes sites where an artery that nourishes the pancreas is connected to arteries that nourish tissues other than the pancreas, the sites being located upstream and downstream of the artery that nourishes the pancreas; a drug administration section which, in a state that an occlusion area that isolates from other tissues the pancreas as well as arteries and veins performing a blood supply and discharge to/from the pancreas is formed by each occlusion section, recovers a liquid upstream of the first vein occlusion section and supplies the recovered liquid to the artery that nourishes the pancreas, the upstream and downstream of which are occluded by the artery occlusion section by using a drug administration pump; a systemic circulation section which, in a state that the occlusion area is formed, recovers a liquid upstream of the second vein occlusion section and feeds the recovered liquid into a systemic circulation different from the occlusion area by using a systemic circulation pump; and a control device which controls the systemic circulation pump so as to recover the liquid upstream of the second vein occlusion section at a predetermined flow rate.

Having such a configuration can prevent the venous blood flowing from collateral pathways outside the pancreas into the second vein from merging into the first main vein into which the venous blood from the pancreas flows. Thus, it can be prevented that blood circulating in the occlusion area isolated for administering a drug to the pancreas is increased in amount by the venous blood from collateral pathways outside the pancreas, and overflown and leaked out of the occlusion area together with the drug.

Further, the control device for controlling the systemic circulation pump so as to recover the liquid at a predetermined flow rate is provided, thus the venous blood flowing from collateral pathways outside the pancreas into the second vein is almost completely returned to the systemic circulation and prevented from being mixed into the occlusion area isolated for administering a drug to the pancreas. As a result, blood mixed with a drug can be strictly prevented from leaking out of the occlusion area isolated for administering a drug to the pancreas.

Therefore, by using the pancreas perfusion apparatus of the present invention, it becomes possible to use a drug having strong side effects on normal tissues, including a gene therapeutic drug using a vector, thereby making it possible to give an effective treatment having almost no side effects to intractable pancreatic diseases such as pancreatic cancer.

Remarkably, considering that a truly effective therapeutic method for pancreatic cancer, one of cancers having a highest mortality rate, has been unknown to date, the pancreas perfusion apparatus of the present invention opens up the possibility of a long-awaited complete cure of pancreatic cancer.

Further, not only pancreatic cancer can be treated, but also being treated without side effects, thus a patient's physical burden is significantly reduced and a patient's QOL is significantly improved.

Further, unnecessary drug consumption caused by leakage to the systemic circulation is avoided, thus even when a very expensive drug such as a gene therapeutic drug is used, a drastic increase in costs in clinical tests and treatments can be prevented.

In this configuration, the drug may be a gene therapeutic drug used for a gene therapy, and the control device may include: an administration signal input section for receiving an administration signal indicating that the drug is administered to the drug administration section; a drug perfusion stopping section for stopping the driving of the drug administration pump at a time point when a first time passes from a time of receiving the administration signal, the administration signal being received during the driving of the drug administration pump and the systemic circulation pump; and a notification section for notifying an end time of the percutaneous isolated pancreas perfusion at a time point when a second time passes after the driving of the drug administration pump is stopped.

A gene therapy includes some of steps which depend on in vivo biological functions, including a step in which an administered gene is incorporated into a target cell, a step in which the gene is properly transcribed and translated in the cell, and a step in which a translated protein becomes a functional protein by having a proper conformation to function inside the cell or be secreted outside the cell. Thus, a gene therapy is featured by the fact that it takes a longer time for a gene-based drug to be functional as compared to a conventional biomaterial-based drug.

Regarding this matter, in the present invention, the driving of the drug administration pump is stopped by the control device when the first time passes after the administration of the drug. Since the perfusion of the gene therapeutic drug in the pancreas is stopped, the gene therapeutic drug is exposed to cells while remaining still in each portion of the pancreas, thereby making it possible to transfer a gene as the gene therapeutic drug.

According to a conventional arterial infusion therapy and the like, a blood flow is generated in arteries and veins by the heart's pulsation of a patient himself/herself and exposure of the gene therapeutic drug to cells in a lesion is not achieved, thus causing a very low level of a gene transfer efficiency. In contrast, according to the present invention, a blood flow itself is stopped in the occlusion area isolating arteries and veins performing a supply and discharge of blood to/from the pancreas, thus enabling gene expression of the gene therapeutic drug.

Further, the notification section for notifying the end time of the percutaneous isolated pancreas perfusion at a time point when the second time passes after the driving of the drug administration pump is stopped is provided, thus a completion time of incorporation of the gene therapeutic drug into cells in a lesion can be speculated by an operator.

The predetermined flow rate may be 150 ml/min. or more.

With such a configuration, the venous blood flowing from collateral pathways outside the pancreas into the second vein is almost completely returned to the systemic circulation and almost completely prevented from being mixed into the occlusion area isolated for administering a drug to the pancreas. As a result, the blood mixed with the drug can be strictly prevented from leaking out of the occlusion area isolated for administering a drug to the pancreas.

It may be that the first vein is the portal vein, the first vein occlusion section is arranged in the main portal vein in the vicinity of a merging portion of the splenic vein and the superior mesenteric vein, and the second vein is the superior mesenteric vein. The artery occlusion section may include, at least, a first artery occlusion section which occludes the common hepatic artery located upstream of a branching portion of the proper hepatic artery and the gastroduodenal artery, a second artery occlusion section which occludes the main celiac artery located upstream of a branching portion of the common hepatic artery, the left gastric artery, and the splenic artery, and occlusion sections which occlude the left gastric artery and the splenic artery each at a distal portion separated from a branching portion of the artery nourishing the pancreas.

Having such a configuration can strictly prevent a leakage of blood containing the drug out of the pancreas during the percutaneous isolated pancreas perfusion.

The artery occlusion section may further include a dorsal pancreatic artery occlusion section which occludes the dorsal pancreatic artery branched from the superior mesenteric artery.

There is an individual difference among living bodies in a branching structure and the like of arteries and veins performing a supply and discharge of blood to/from the pancreas. For a patient whose dorsal pancreatic artery is branched from the superior mesenteric artery, a leakage of blood containing the drug out of the occlusion area isolating arteries and veins performing a supply and discharge of blood to/from the pancreas can be strictly prevented by further providing the dorsal pancreatic artery occlusion section which occludes the dorsal pancreatic artery branched from the superior mesenteric artery.

The control device may control the systemic circulation pump so as to recover a liquid upstream of the second vein occlusion section at a flow rate of 300 ml/min. or more when a body weight of the patient is 50 kg or more.

With such a configuration, the venous blood flowing from collateral pathways outside the pancreas into the second vein is almost completely returned to the systemic circulation and almost completely prevented from being mixed into the occlusion area isolated for administering a drug to the pancreas. As a result, blood mixed with the drug can be strictly prevented from leaking out of the occlusion area isolated for administering a drug to the pancreas.

The first time may be a time required for the gene therapeutic drug to reach all the regions of the pancreas and the second time may be 15 minutes or more.

An in vitro study and the like show that a gene therapeutic drug needs to be exposed to cells for about 15 minutes until a gene is introduced. Thus, in the present invention, having such a configuration makes it possible to incorporate a gene therapeutic drug into cells in a lesion inside the pancreas.

The control device may control the drug administration pump so that a flow rate of the liquid recovered from the upstream side of the first vein occlusion section is higher than that of the liquid supplied to the artery by 0 to 15 ml/min.

Having such a configuration can strictly prevent a leakage of blood mixed with the drug out of the occlusion area isolated for administering a drug to the pancreas.

Effects of Invention

According to the present invention, the venous blood flowing from collateral pathways outside the pancreas into the second vein is prevented from merging into the first main vein into which the venous blood from the pancreas flows. Thus, it can be prevented that blood circulating in the occlusion area isolated for administering a drug to the pancreas is increased in amount by the venous blood from collateral pathways outside the pancreas, and overflown and leaked out of the occlusion area together with the drug.

Further, the control device for controlling the systemic circulation pump so as to recover the liquid upstream of the second vein occlusion section at a predetermined flow rate is provided, thus the venous blood flowing from collateral pathways outside the pancreas into the second vein is almost completely returned to the systemic circulation and almost completely prevented from being mixed into the occlusion area isolated for administering a drug to the pancreas. As a result, blood mixed with the drug can be strictly prevented from leaking out of the occlusion area isolated for administering a drug to the pancreas.

Therefore, by using the pancreas perfusion apparatus of the present invention, it becomes possible to use a drug having strong side effects on normal tissues including a gene therapeutic drug using a vector, thereby making it possible to give an effective treatment having almost no side effects to intractable pancreatic diseases such as pancreatic cancer.

Remarkably, considering that a truly effective therapeutic method for pancreatic cancer, one of cancers having a highest mortality rate, has been unknown to date, the pancreas perfusion apparatus of the present invention opens up the possibility of a long-awaited complete cure of pancreatic cancer.

Further, not only pancreatic cancer can be treated, but also being treated without side effects, thus a patient's physical burden is significantly reduced and a patient's QOL is significantly improved.

Further, unnecessary drug consumption caused by a leakage to the systemic circulation is avoided, thus even when a very expensive drug such as a gene therapeutic drug is used, a drastic increase in costs in clinical tests and treatments can be prevented.

DESCRIPTION OF EMBODIMENTS

Hereinafter, a pancreas perfusion apparatus according to one embodiment of the present invention, a method for controlling the same, and a method for pancreas perfusion will be described with reference to FIG. 1 to FIG. 4.

It is noted that, in the present description, a liquid as referred to in embodiments is a general term of all liquids that fill vascular systems or interspaces of tissues/cells in an animal body, and includes body fluids such as blood, lymph, and cerebrospinal fluid. Further, drugs such as a gene therapeutic drug are also included in some cases.

Further, in the present description, explanation is given to an example that the pancreas perfusion apparatus and the pancreas perfusion method are applied to the pancreas, however the present invention is not limited thereto and can be applied to other organs and tissues by changing occlusion sites, liquid aspirating sites and liquid feeding sites, perfusion time, and the like according to organs and tissues.

Figure 1:
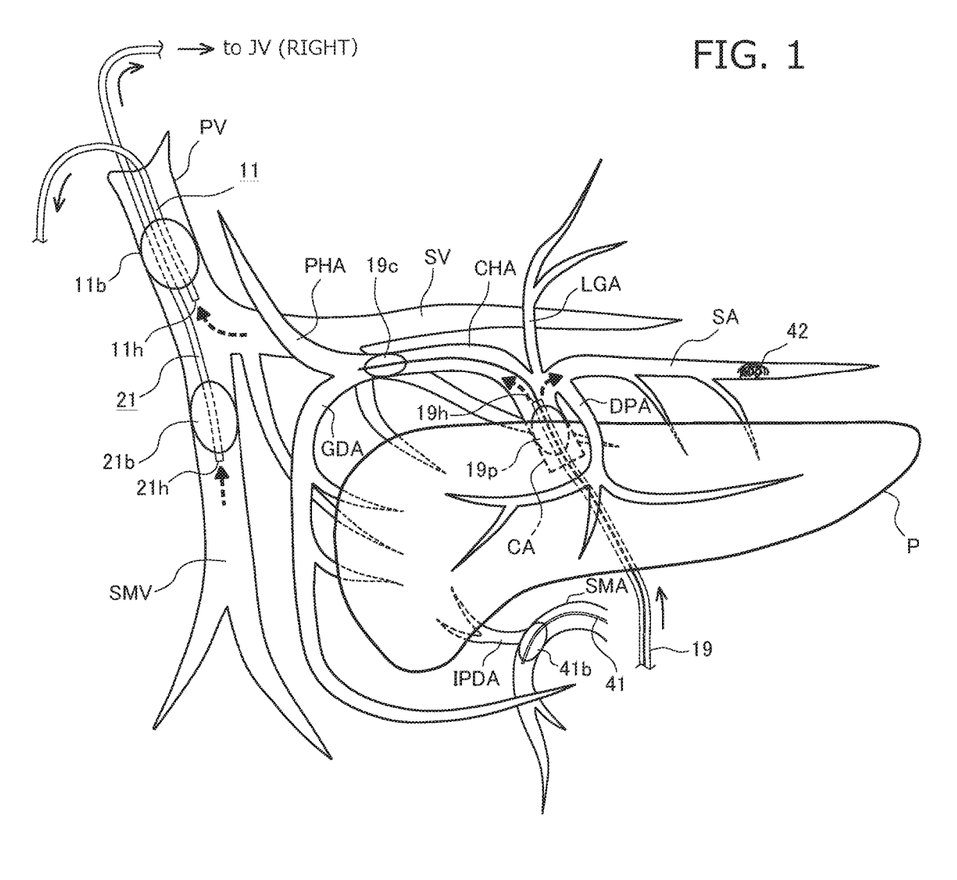
FIG. 1 is a schematic view illustrating the pancreas and its surrounding arteries and veins to which percutaneous isolated pancreas perfusion using a pancreas perfusion apparatus according to one embodiment of the present invention is applied.

As shown in FIG. 1, the pancreas perfusion apparatus according to the present embodiment is a device for perfusing a gene therapeutic drug containing a tumor suppressor gene, such as mda-7/IL-24, in the pancreas by a percutaneous isolated pancreas perfusion method.

Example of diseases to which the pancreas perfusion apparatus and the pancreas perfusion method of the present invention are applied include pancreatic cancer including invasive ductal carcinoma as a representative pancreatic cancer, as well as pancreatic neuroendocrine tumor, intraductal papillary mucinous neoplasm, mucinous cystic neoplasm, acinic cell carcinoma, metastatic pancreatic cancer, and the like, diabetes, and pancreatitis. Further, among pancreatic cancer, the device and method can be applied to any sites of cancer, including uncinate process pancreatic cancer, pancreatic head cancer, pancreatic body cancer, and pancreatic tail cancer.

A gene therapeutic drug can be classified into two types according to a gene transfer method: an in vivo gene therapy in which a gene for therapy is directly administered into a living body; and an ex vivo gene therapy in which a target cell is taken out of a body once, ant then the cell is transferred with a gene and returned to the body again as a cell for therapy. Either type of drugs can be used as the gene therapeutic drug of the present invention.

Among genes used in the in vivo gene therapy, mda-7/IL-24, which is known as a tumor suppressor gene and inhibits the growth of tumors by inducing apoptosis when introduced into tumor cells, as well as various tumor suppressor genes, such as p53, interferon β, herpes virus thymidine kinase (HSV-tk), interferon-β, interleukin-12 (IL-12), and a tumor suppressor factor REIC (Reduced Expression in Immortalized Cells)/Dickkopf-3 (Dkk-3) can be used.

Further, although these genes may be used as they are, they are preferably used by being inserted into a vector, such as a retrovirus vector, a lentivirus vector, an adenovirus vector, an adeno-associated virus vector, a Sendai virus vector, and a plasmid vector, so that a gene transfer efficiency is increased.

Further, as the ex vivo gene therapy, an adoptive immunogene therapy using a own T cell, in which a T-cell receptor gene recognizing a cancer antigen or a chimera receptor gene combining an antigen recognition site of a cancer antigen specific antibody and a T-cell activation region is transferred, may be applicable in the present invention.

As an example of TCR gene therapy in which a T-cell receptor gene recognizing a cancer antigen is transferred to a patient's T cell, there is known a therapy in which a T-cell antigen receptor gene recognizing a MAGE-A4 antigen is transduced into a peripheral blood-derived lymphocyte isolated from a cancer patient to be treated in vitro using a retroviral vector and then introduced into the patient by infusion.

It is noted that, in the present embodiment, explanation is given to an example that the pancreas perfusion apparatus and the pancreas perfusion method are applied to the percutaneous isolated pancreas perfusion of a gene therapeutic drug, however the present invention is not limited thereto, and, as a drug, all kinds of drugs including a drug consisting of a low molecular organic compound, a hormone drug such as erythropoietin, a protein-based drug such as an antibody drug (a biotechnology-based drug), an anticancer drug, and a nucleic acid-based drug such as antisense, aptamer, siRNA, miRNA, and decoy, can be used.

<<Main Configuration of Pancreas Perfusion Apparatus>>

Figure 2:
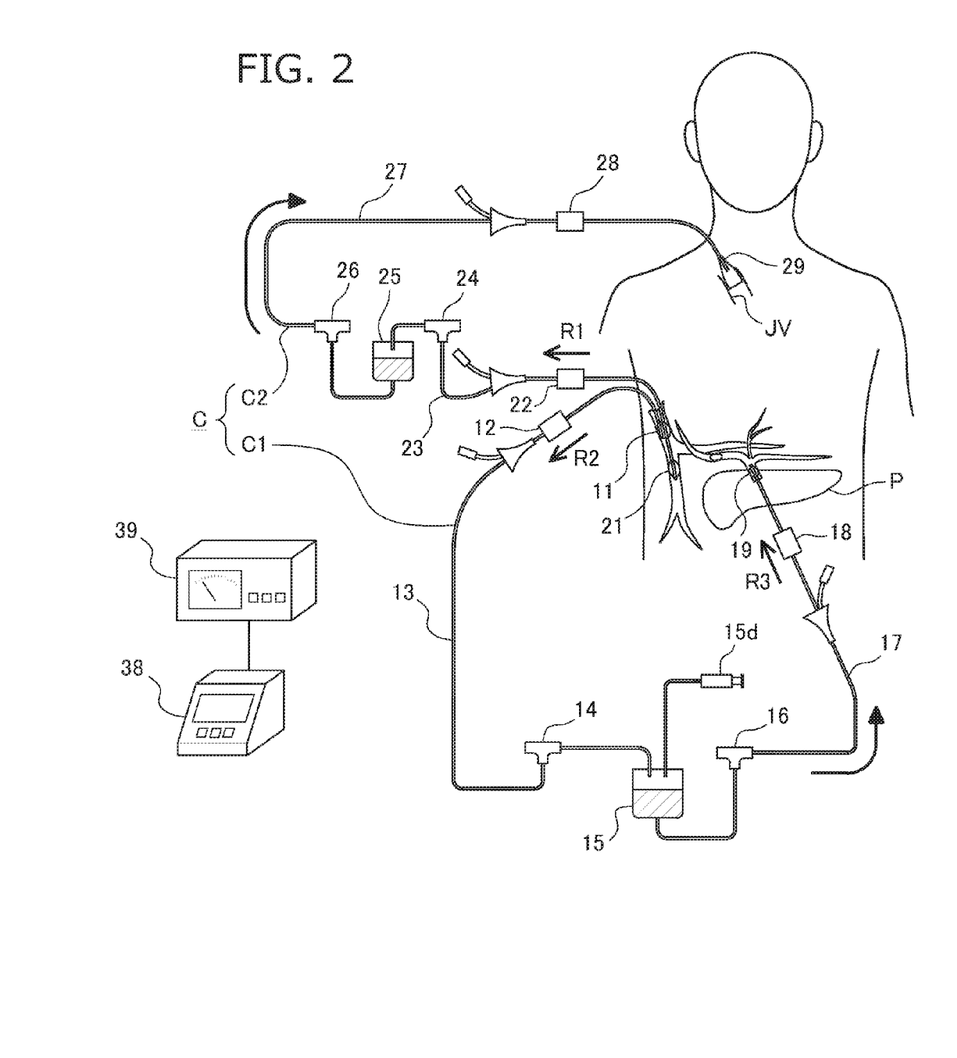
FIG. 2 is an explanatory diagram illustrating the pancreas perfusion apparatus according to one embodiment of the present invention.
Figure 3:
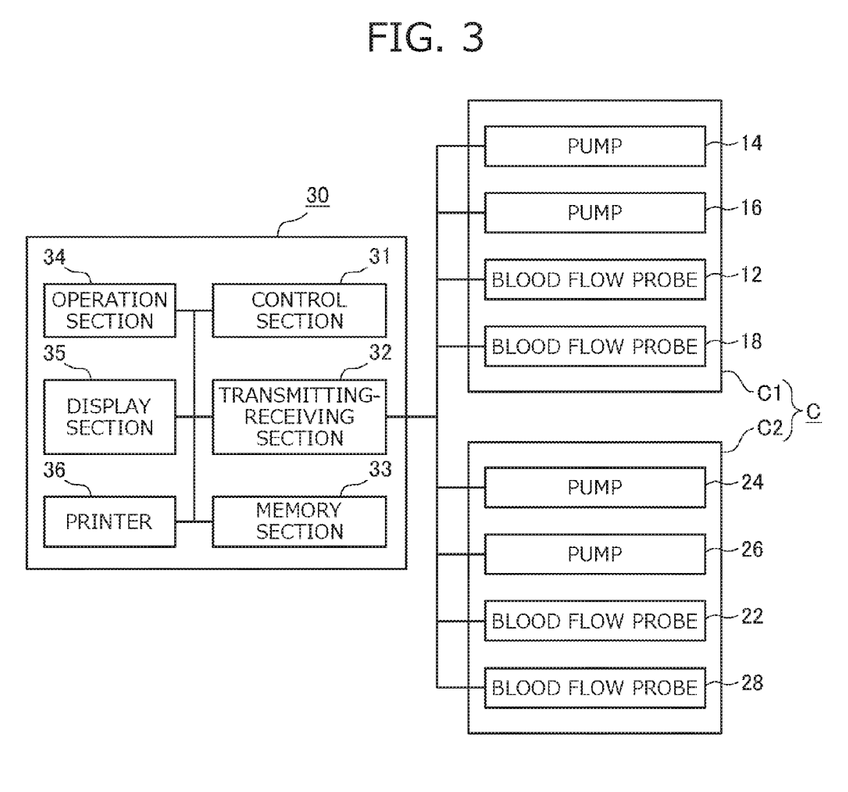
FIG. 3 is a block diagram illustrating a control system of the pancreas perfusion apparatus according to one embodiment of the present invention.

As shown in FIG. 1 to FIG. 3, the pancreas perfusion apparatus of the present embodiment includes, as a main component, a drug administration circuit C1 for administering a gene therapeutic drug (hereinafter referred to as a "drug"), a systemic circulation circuit C2 for feeding blood aspirated from a superior mesenteric vein SMV into a right jugular vein JV, a controller 30 for controlling each component contained in the drug administration circuit C1 and the systemic circulation circuit C2, a balloon catheter 41 for preventing a leakage of the drug to other organs, and an embolic coil 42.

The drug administration circuit C1 is a circuit for circulating blood to an artery that nourishes a pancreas P and a vein into which blood is discharged from the pancreas P, the circuit being used for filling the drug.

The drug administration circuit C1 includes a balloon catheter 11 positioned in a main portal vein PV to which blood from the pancreas P flows out, a blood flow probe 12 for measuring a flow rate of the blood aspirated from the balloon catheter 11, a tube 13 for the blood aspirated from the balloon catheter 11, a pump 14 for feeding the blood aspirated from the balloon catheter 11 to a reservoir 15, the reservoir 15 for storing the blood aspirated from the balloon catheter 11, a drug port 15d for mixing a drug into the reservoir 15, a pump 16 for sending out the blood from the reservoir 15, a tube 17 for the blood flowing into a double coaxial balloon catheter 19, a blood flow probe 18 for measuring a flow rate of the blood fed to the double coaxial balloon catheter 19, and the double coaxial balloon catheter 19, which includes a micro balloon 19c for occluding a common hepatic artery CHA upstream of a proper hepatic artery PHA that nourishes a liver and a gastroduodenal artery GDA that nourishes a pylorus and a duodenum, and a parent balloon 19p for occluding a site through which blood flows in a dorsal pancreatic artery DPA that nourishes the pancreas P, and supplies blood containing the drug to the dorsal pancreatic artery DPA.

The balloon catheter 11 is a known separate-type balloon catheter and includes a balloon 11b as an inflation body and a tube including an inflation fluid lumen which has the balloon attached to a distal portion and circulates a gas or a liquid for inflating the balloon through an inner space disposed between an inner tube and the catheter, a guide wire lumen through which a guide wire for guiding the balloon catheter to a lesion is inserted, and a blood-feeding lumen for feeding patient's blood. The blood-feeding lumen includes an opening 11h for circulating blood on the distal portion farther than the balloon 11b.

The blood flow probes 12 and 18 are a known blood flow probe such as an ultrasonic blood flow meter and connected to a blood flow meter 39 via a cable not illustrated. A signal of a blood flow rate detected by the blood flow probes 12 and 18 is sent to the blood flow meter 39.

The double coaxial balloon catheter 19 is a known double coaxial balloon catheter and includes a parent catheter and a child catheter.

The parent catheter includes a parent balloon 19p as an inflation body, disposed at the distal portion, an inflation fluid lumen, a guide wire lumen, a blood-feeding lumen, and a child catheter lumen through which the child catheter is inserted. The blood-feeding lumen includes an opening 19h for circulating blood on the distal portion farther than the parent balloon 19p.

The child catheter includes a micro balloon 19c as an inflation body, disposed at the distal portion and an inflation fluid lumen, and is inserted in the child catheter lumen of the parent catheter in a manner that the micro balloon 19c is located at the distal portion of the parent balloon 19p.

The systemic circulation circuit C2 is a circuit for returning a venous blood flown into the superior mesenteric vein SMV from collateral pathways outside the pancreas P flows to the systemic circulation. Since the superior mesenteric vein SMV is merged with a splenic vein SV at the downstream, this circuit is formed to prevent the venous blood flown into the superior mesenteric vein SMV from collateral pathways outside the pancreas P from flowing into the splenic vein SV.

When a venous blood containing the drug, flowing into the portal vein PV, is aspirated from the opening 11h of the balloon catheter 11 while the portal vein PV is occluded, a venous blood containing no drugs, flown into the superior mesenteric vein SMV from collateral pathways, also flows toward the opening 11h. Thus, an amount of blood flowing into the opening 11h is increased and blood, in which the venous blood containing the drug and the venous blood flown from collateral pathways are mixed, overflows at the splenic vein SV side, thereby causing a leakage of blood from the drug administration circuit C1 to the outside of the circuit.

Thus, by forming the drug administration circuit C2 that aspirates the venous blood containing no drugs, flown into the superior mesenteric vein SMV from collateral pathways outside the pancreas P, at the upstream of a merging portion between the superior mesenteric vein SMV and the splenic vein SV, and returns the venous blood to the jugular vein, an amount of the blood flowing to the suction side of the drug administration circuit C1 is reduced. As a result, a leakage of the blood containing the drug from the drug administration circuit C1 is almost completely prevented.

The systemic circulation circuit C2 includes a balloon catheter 21 positioned in the superior mesenteric vein SMV into which the blood from collateral pathways outside the pancreas P flows, a blood flow probe 22 for measuring a flow rate of the blood aspirated from the balloon catheter 21, a tube 23 for the blood aspirated from the balloon catheter 21, a pump 24 for feeding the blood aspirated from the balloon catheter 21 to a reservoir 25, the reservoir 25 for storing the blood aspirated from the balloon catheter 21, a pump 26 for sending out the blood from the reservoir 25, a tube 27 for the blood flowing toward a cannula 29, a blood flow probe 28 for measuring a flow rate of the blood sent out to the cannula 29, and the cannula 29 for supplying the blood containing no drug to the jugular vein JV.

The balloon catheter 21, having the same configuration as the balloon catheter 11, includes a balloon 21b and an opening 21h.

The blood flow probes 22 and 28 are a known blood flow probe such as an ultrasonic blood flow meter and connected to a blood flow meter 39 via a cable not illustrated. A signal of a blood flow rate detected by the blood flow probes 22 and 28 is sent to the blood flow meter 39.

The controller 30 includes a control section 31, a transmitting-receiving section 32, a memory section 33, an operation section 34, a display section 35, and printer 36.

The control section 31 is constituted of a CPU and outputs an instruction signal, based on a driving program stored in the memory 33 in advance, for driving each of the pumps 14, 16, 24, and 26, the blood flow meter 39, and each of the blood flow probes 12, 18, 22, and 28 of the drug administration circuit C1 and the systemic circulation circuit C2.

Further, driving information is input to the control section 31 from each of the pumps 14, 16, 24, and 26 and information on a blood flow rate detected by each of the blood flow probe 12, 18, 22, and 28 is input to the control section 31 from the blood flow meter 39.

The transmitting-receiving section 32 is a section for transmitting and receiving information to/from each of the devices, which sends a control signal from the control section 31 to each of the devices, and receives the driving information, measurement values of the blood flow rate, and the like from each of the devices and then sends them to the control section 31.

The operation section 34 is a section for accepting an input from a user. Further, the display section 35 is composed of, for example, a liquid crystal panel, and displays the driving information of each of the devices, information related to a control condition input, and the like. The display section 35 can also perform an alarm display when an abnormality occurs.

The memory 33 stores in advance a control program for executing the gene therapeutic perfusion method of the present embodiment, control conditions required for the control section 31 to perform a driving control of each of the devices, and the like. The control section 31 takes out information input from the operation section 34 from the memory 33, or stores data input from operation section 34 in the memory 33, while each of the devices is driven.

The embolic coil 42 is a known micro coil for blood vessel embolization and used for preventing a leakage of the drug into organs other than the pancreas P. The embolic coil 42 occludes the splenic artery SA at the distal site farther than the branching point of the artery that nourishes the pancreas P.

It is noted that a left gastric artery LGA is usually branched from the proximal portion of a celiac artery CA. Since the branching point is close to the celiac artery CA, the left gastric artery LGA is occluded by the parent balloon 19p that occludes the celiac artery CA, thus occlusion of the left gastric artery LGA is not necessary. However, for a patient whose left gastric artery LGA is branched at a position apart from the celiac artery CA due to a individual difference among living bodies, the left gastric artery LGA may be occluded at the proximal portion of the branch point of the celiac artery CA by an embolic coil not illustrated. It is noted that the left gastric artery LGA merges with the portal vein PV after nourishing the stomach.

Further, a superior mesenteric artery SMA is occluded by a balloon 41b of the balloon catheter 41 at a position branched into a first jejunal artery J1 not illustrated. It is known that there is a large individual difference among living bodies in a branching pattern of the jejunal artery J1 and a positional relationship thereof to the superior mesenteric artery SMA, as such there are several variations. However, in any of variations, it is known that the jejunal artery J1 branches an inferior pancreaticoduodenal artery IPDA, thus as shown in FIG. 1, by occluding the superior mesenteric artery SMA at a position branched into an inferior pancreaticoduodenal artery IPDA and the jejunal artery J1, a nutrient supply from the pancreas P to others can be shut off and more drugs can be spread over the whole pancreas P.

<<Percutaneous Isolated Pancreas Perfusion Therapy Using Pancreas Perfusion Apparatus>>

A percutaneous isolated pancreas perfusion therapy as the pancreas perfusion method realized by the pancreas perfusion apparatus of the present embodiment is explained based on FIG. 1.

In the present embodiment, examples of applying the pancreas perfusion apparatus to a percutaneous isolated pancreas perfusion therapy for pancreatic cancer is explained, however, it can be applied to other organs, tissues, and the like, as well as other diseases.

All operative procedures are performed under sterile conditions and general anesthesia. The patients are placed in the supine position, and general anesthesia is induced using a 12.5 mg/kg intramuscular injection of ketamine hydrochloride (Ketalar Intramuscular 500 mg), and maintained with 5% sevoflurane administered via a mask. An endrotracheal tube may be inserted and anesthesia may be maintained with sevoflurane (5%), nitrous oxide (3 L/min.), and oxygen (3 L/min.).

During the surgical procedures, peripheral arterial oxygen saturation is maintained above 95%. The patient is monitored with circulatory dynamics by continuously recording electrocardiogram during the procedures. The left axillary artery and the left jugular vein of the patient are exposed and cannulas (5-French) are inserted into each vessel. Further, the right jugular vein JV is also exposed and a cannula 29

(9-French) is inserted into it. The cannula in the left axillary artery is used to monitor blood pressure during the procedures; the cannula in the left jugular vein is used to collect blood samples and administer Ringer's solution by intravenous drip infusion. The cannula 29 in the right jugular vein JV is used to return blood via the superior mesenteric vein SMV to the systemic circulation.

An isolated pancreas circuit C shown in FIG. 1 and FIG. 2 is set as follows.

Drug injection devices for injecting a gene therapeutic drug (hereinafter referred to as a "drug") into the celiac artery CA are arranged as follows.

A cannula of 8-French is inserted into the right common femoral artery and superior mesenteric arteriography and celiac arteriography is performed for anatomical mapping.

The splenic artery SA, in which the distal site of the origin of the pancreatic branch is located, is embolized with the embolic coil 42 to prevent leakage of drugs.

If the dorsal pancreatic artery DPA originates from the superior mesenteric artery SMA, the dorsal pancreatic artery DPA is occluded by a balloon catheter not illustrated to unify feeding arteries to the pancreas P.

The parent balloon 19p of the double coaxial balloon catheter 19 of 8-French is positioned in the main celiac artery CA and the child catheter is advanced through this parent catheter to the distal site of the common hepatic artery CHA, so that the micro balloon 19c of the child catheter is positioned at a position capable of occluding the proper hepatic artery PHA and the gastroduodenal artery GDA. Further, the balloon 41b of the balloon catheter 41 is positioned in the superior mesenteric artery SMA at a position branched into the inferior pancreaticoduodenal artery IPDA and the first jejunal artery J1. The pancreas P is infused via the opening 19h of the double coaxial balloon catheter 19 of 8-French positioned in the main celiac artery CA.

Drug suction devices for aspirating the drug from the portal vein PV are arranged as follows.

Two intrahepatic portal branches are punctured under an ultrasonographic guidance and two cannulas of 12-French are inserted into the portal vein PV along with a guide wire. Two 12-French balloon catheters 11 and 21 with a 30 mm-balloon are inserted into each of the cannulas and a balloon 11b and a balloon 21b are positioned in the main portal vein PV and the superior mesenteric artery SMA, respectively. Among these balloon catheters, the balloon catheter 21 positioned in the superior mesenteric artery SMA is used to aspirate blood from the superior mesenteric vein SMV and to return the blood to the systemic circulation via the cannula 29 of the right jugular vein JV, while the balloon catheter 11 positioned in the main portal vein PV is used to aspirate blood with the drug from drainage veins of the pancreas P.

Accordingly, the isolated pancreas circuit C including the drug administration circuit C1 for injecting the blood containing the drug, aspirated from the main portal vein PV, into the main celiac artery CA and the systemic circulation circuit C2 for injecting the blood aspirated from the superior mesenteric vein SMV into the right jugular vein JV is formed.

A perfusion technique is as follows. First, systemic heparinization (120 U/kg or more) is performed. A dose of heparin may be such an amount that an activated clotting time (ACT) becomes 250 seconds or more. Subsequently, the parent balloon 19p of the celiac artery CA and the micro balloon 19c of the common hepatic artery CHA are inflated in this order.

Next, the balloon 41b positioned in the superior mesenteric artery SMA at the level branched into the inferior pancreaticoduodenal artery IPDA, depending on an individual difference among patients, may be inflated. After occluding the superior mesenteric artery SMA at the level branched into the inferior pancreaticoduodenal artery IPDA by inflating the balloon 41b, it has been found that a leakage from the isolated pancreas circuit C is sometimes effectively prevented, but sometimes not, depending on an individual difference. Thus, occlusion by the balloon 41b may be performed or not performed, depending on an individual difference.

Then, the balloon 21b of the superior mesenteric vein SMV and the balloon 11b of the main portal vein PV are inflated in this order. Isolated pancreatic arteriography is performed while driving the pumps 14, 16, 24 and 26, and the blood flow probes 12, 18, 22 and 28 in order to confirm that the isolated pancreas circuit C is properly closed and the percutaneous isolated pancreas perfusion system is functioning. After confirming the patency of the system by the isolated pancreatic arteriography, a drug (1.5 mg/kg) is injected into the reservoir 15 from the drug port 15d to perform the percutaneous isolated pancreas perfusion therapy.

In the percutaneous isolated pancreas perfusion therapy, after injecting the drug, for a first time of 30 seconds to 1 minute until the drug is spread over the entire lesion of the pancreas P, all of the pumps 14, 16, 24 and 26 are kept driven, thereby performing perfusion of both of the drug administration circuit C1 and the systemic circulation circuit C2.

Subsequently, when the drug is spread over the entire lesion of the pancreas P, the pumps 14 and 16 of the drug administration circuit C1 are stopped, while the pumps 24 and 26 of the systemic circulation circuit C2 are continuously driven without being stopped, so that a state, in which perfusion of the drug administration circuit C1 is stopped and perfusion of the systemic circulation circuit C2 is continued, is maintained for a second time, that is, for at least 15 minutes, preferably 15 to 30 minutes.

It is noted that the second time varies depending on the type of vectors used for a gene therapeutic drug. For example, the second time may be set to about 15 to 20 minutes in case of using retrovirus vectors having a high transfer efficiency, however the second time is set to about 30 minutes to 1 hour in case of using adeno-associated virus vectors and the like having low toxicity.

Further, the second time is also influenced by the concentration of a gene therapeutic drug. When the concentration of a gene therapeutic drug in blood is high, the second time during which the pancreas P is exposed to the gene therapeutic drug may be shorten. Thus, the second time may be set to about 5 minutes depending on the concentration of a gene therapeutic drug.

It is noted that both of the pumps 12 and 24 for aspirating blood maintain their aspiration pressure at <100 mmHg to avoid hemolysis of blood.

Finally, the cannula 29, the balloon catheters 11 and 21, and the double coaxial balloon catheter 19 are removed, thereby completing the percutaneous isolated pancreas perfusion therapy.

It is noted that a branch path switchable by a valve may be formed in the tube 13 of the drug administration circuit C1 and a filter for removing the drug from blood may be arranged in such a branch path. After the completion of the percutaneous isolated pancreas perfusion therapy, the valve of the drug administration circuit C1 is switched, then a step of passing blood containing the drug, aspirated from the main portal vein PV, through the filter to remove the drug from the blood and injecting the blood into the main celiac artery CA may be performed for 3 to 5 minutes.

It is noted that, both in the drug administration circuit C1 and the systemic circulation circuit C2, an injection rate into the main celiac artery CA and the right jugular vein JV is set to 60 ml/min. or less, preferably 45 ml/min. or less, more preferably 40 ml/min. or less, and more preferably 36 ml/min. or less in order to prevent liquefactive necrosis and suppress damages to the pancreas.

It is noted that this injection rate was determined based on a result of experiment of the percutaneous isolated pancreas perfusion therapy conducted using nine female swine, in which an isolated pancreas circuit C was formed in the same manner as shown in FIG. 1 and FIG. 2, and a blood injection rate was set to three different levels, 60 ml/min. (Group 1: n=3), 80 ml/min. (Group 2: n=3), and 100 ml/min. (Group 3: n=3).

In this experiment, in Group 1, the appearance was normal in the pancreas, as well as the liver, the spleen, the duodenum, the small intestine and the colon, and ischemic changes or edematous changes in the pancreas were not observed by histological evaluation. Further endovascular clot was not observed. However, according to close observation, liquefactive necrosis occurred in some tissues. Further, in Group 2, edematous appearance was observed in the pancreas in one out of three animals. Although ischemic changes were not observed, edematous changes were observed in the pancreas in two animals by histological evaluation. Ischemic changes or edematous changes were not observed in the liver, the duodenum, the small intestine or the colon. In Group 3, edematous appearance was observed in the pancreas in all three animals, and edematous changes were observed in the pancreas in all three animals by histological evaluation. Ischemic changes or edematous changes were not observed in the liver, the duodenum, the small intestine or the colon.

Subsequently, the same experiment was performed using female swine, in which the blood flow rate was set to 40 ml/min., to find that liquefactive necrosis did not occur at all.

<<Processing Flow of Pancreas Perfusion Apparatus>>

Figure 4:
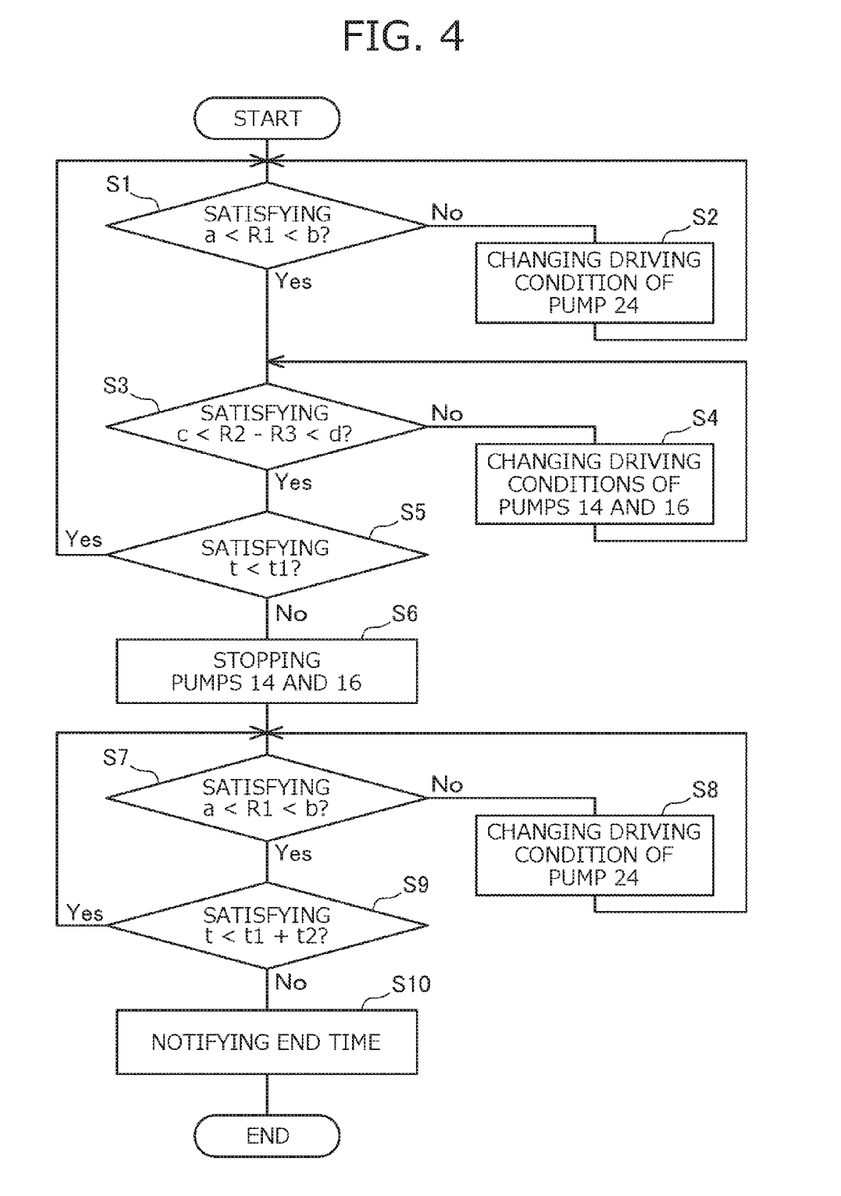
FIG. 4 is a flowchart illustrating a control of a controller of the pancreas perfusion apparatus according to one embodiment of the present invention.

Next, processing of the pancreas perfusion apparatus by the controller 30 will be explained based on a flowchart in FIG. 4. Processing of the flowchart in FIG. 4 is controlled by the control section 31 of the controller 30.

First, a first time t1 during which blood both in the drug administration circuit C1 and the systemic circulation circuit C2 is circulated after a drug is administered and a second time t2 during which only blood in the systemic circulation circuit C2 is circulated in a state that circulation of blood of the drug administration circuit C1 is stopped after the first t1 passes are set to the controller 30 using the operation section 34 by an operator.

Further, regarding a flow rate R1 of the blood aspirated from the balloon catheter 21 during the operation and a difference (R2−R3) between a flow rate R2 of the blood aspirated from the balloon catheter 11 and a flow rate R3 of the blood returned from the double coaxial balloon catheter 19 from a time when the drug is administered until the lapse of the time t1, values thereof to be maintained during the operation of the gene therapeutic drug perfusion method are set to the controller 30 using the operation section 34 by an operator.

As a setting value of R1, a lower limit value a and an upper limit value b are set so that R1 is maintained in a range of a<R1<b. Further as a setting value of R2−R3, a lower limit value c and an upper limit value d of the difference between R2 and R3 are set so that the difference between R2 and R3 is maintained in a range of c<R2−R3<d from a time when the drug is administered until the lapse of the time t1.

Here, an appropriate value of R1 differs according to the patient's weight, however the value needs to be set to at least 150 ml/min. in order to prevent a leakage of the drug from the drug administration circuit C1.

When the patient's weight is 50 kg or more, the value of a may be set to 300 ml/min. or more, preferably 320 to 370 ml/min., while the value of b may be set to 380 ml/min. or more, preferably 390 to 420 ml/min. However, for a small-sized patient whose weight is less than 50 kg, the value of a may be set to 200 ml/min. or more, preferably 220 to 270 ml/min., while the value of b may be set to 280 ml/min. or more, preferably 290 to 320 ml/min.

Further, when R1 is set to a sufficiently large value, R2 and R3 may be set to approximately the same values with R2 not being smaller than R3. The value of c may be set to 0 or more, preferably 1 to 5 ml/min, while the value of d may be set to 5 ml/min. or more, preferably 5 to 10 ml/min.

It is noted that, in the present embodiment, R1 is set to a sufficiently large value, thus R2 and R3 may be set to the same values. However, by setting R2 to be larger than R3 only by 5 ml/min., a leakage of the drug out of the pancreas can be further suppressed.

Further, in the present embodiment, the lower limit values and the upper limit values of R1 and R2−R3 are set, however it is not necessary to set and control the lower limit value and the upper limit value of R2−R3.

After each medical appliance such as the cannula 29, the balloon catheters 11 and 21, and the double coaxial balloon catheter 19 is arranged at a specified position and each device such as the pumps 14, 16, 26, and 26, and the controller 30 is connected and driven, it is confirmed that the drug administration circuit C1 and the systemic circulation circuit C2 are properly closed, blood is properly circulated in the drug administration circuit C1 and the systemic circulation circuit C2, and the percutaneous isolated pancreas perfusion system is functioning. Then, the dug is injected into the reservoir 15 from the drug port 15*d*, and at the same time, a start button not illustrated is pressed by an operator using the operation section 34 of the controller 30.

When the start button not illustrated is pressed, the processing of the flowchart in FIG. 4 is started.

First, in step S1, it is determined if the flow rate R1 of the blood flow probe 22 obtained from the blood flow meter 39 satisfies a<R1<b.

If a<R1<b is not satisfied (step S1: No), it is interpreted that a suction rate of the blood from the superior mesenteric vein SMV in the systemic circulation circuit C2 does not coincide with the set value. Then, in step S2, driving conditions of the pumps 24 and 26 are changed. Specifically, if a<R1 is not satisfied, the flow rates of the pumps 24 and 26 are set to be higher, and if R1<b is not satisfied, the flow rates of the pumps 24 and 26 are set to be lower.

Next, step S1 is repeated to determine again if the flow rate R1 of the blood flow probe 22 obtained from the blood flow meter 39 satisfies a<R1<b.

If a<R1<b is satisfied (step S1: Yes), it is interpreted that the suction rate of the blood from the superior mesenteric vein SMV in the systemic circulation circuit C2 coincides with the set value. Then, in step S3, it is determined if the flow rates R2 and R3 of the blood flow probes 12 and 18 obtained from the blood flow meter 39 satisfy c<R2−R3<d.

If c<R2−R3<d is not satisfied (step S3: No), it is interpreted that the difference between the suction rate of the blood from the main portal vein PV in the drug administration circuit C1 and the introduction rate of the blood into the celiac artery CA does not coincide with the set value. Then, in step S4, driving conditions of the pumps 14 and 16 are changed. Specifically, if c<R2−R3 is not satisfied, the flow rates of the pumps 14 and 16 are set to be higher, and if R2−R3<d is not satisfied, the flow rates of the pumps 14 and 16 are set to be lower.

Next, step S3 is repeated to determine again if the flow rates R2 and R3 of the blood flow probes 12 and 18 obtained from the blood flow meter 39 satisfy c<R2−R3<d.

Next, in step S5, it is determined if a time t at that time point satisfies t<t1.

If t<t1 is satisfied (step S5: Yes), it is interpreted that, after the drug is administered, the time t does not reach the time t1 at which the drug administration circuit C1 should be stopped, and the step S1 is repeated to determine if the flow rate R1 of the blood flow probe 22 obtained from the blood flow meter 39 satisfies a<R1<b.

That is, the processing of step S1 to S4 is repeated until the time t reaches t1.

If t<t1 is not satisfied (step S5: No), that is, if the time 1 is equal to or larger than time t1, it is interpreted that, after the drug is administered, the time t reaches the time t1 at which the drug administration circuit C1 should be stopped. Then, in step S6, driving of the pumps 14 and 16 are stopped.

By this step S6, perfusion of the drug administration circuit C1 is stopped, while perfusion of the systemic circulation circuit C2 is continuously performed.

Nest, in step S7, it is determined if the flow rate R1 of the blood flow probe 22 obtained from the blood flow meter 39 satisfies a<R1<b.

If a<R1<b is not satisfied (step S7: No), it is interpreted that the suction rate of the blood from the superior mesenteric vein SMV in the systemic circulation circuit C2 does not coincide with the set value. Then, in step S8, driving conditions of the pumps 24 and 26 are changed. Specifically, if a<R1 is not satisfied, the flow rates of the pumps 24 and 26 are set to be higher, and if R1<b is not satisfied, the flow rates of the pumps 24 and 26 are set to be lower.

Next, step S7 is repeated to determine again if the flow rate R1 of the blood flow probe 22 obtained from the blood flow meter 39 satisfies a<R1<b.

If a<R1<b is satisfied (step S7: Yes), it is interpreted that the suction rate of the blood from the superior mesenteric vein SMV in the systemic circulation circuit C2 coincides with the set value. Then, in step S9, it is determined if the time t at that time point satisfies t<t1+t2.

If t<t1+t2 is satisfied (step S9: Yes), it is interpreted that, after the drug administration circuit C1 is stopped, the time t does not reach the time t1+t2 at which the percutaneous isolated pancreas perfusion therapy should be ended, and the step S7 is repeated to determine if the flow rate R1 of the blood flow probe 22 obtained from the blood flow meter 39 satisfies a<R1<b.

That is, the processing of step S7 and S8 is repeated until the time t reaches t1+t2.

If t<t1+t2 is not satisfied (step S9: No), that is, if the time t is equal to or larger than time t1+t2, it is interpreted that, after the drug administration circuit C1 is stopped, the time t reaches the time t1+t2 at which the percutaneous isolated pancreas perfusion therapy should be ended. Then, in step S10, an alarm sound notifying an end time of the percutaneous isolated pancreas perfusion therapy is issued as an end time notification, thereby completing the processing.

REFERENCE SIGNS LIST

C: Isolated pancreas circuit
C1: Drug administration circuit
C2: Systemic circulation circuit
CA Celiac artery
CHA: Common hepatic artery
DPA: Dorsal pancreatic artery
JV: Jugular vein
J1: First jejunal artery
GDA: Gastroduodenal artery
LGA: Left gastric artery
P: Pancreas
PHA: Proper hepatic artery
PV: Portal vein
R1, R2, R3: Flow rates
SA: Splenic artery
SMA: Superior mesenteric artery
SMV: Superior mesenteric vein
SV: Splenic vein
11, 21, 41: Balloon catheters
11$b$, 21$b$, 41$b$: Balloons
11$h$, 19$h$, 21$h$: Openings
12, 18, 22, 28: Blood flow probes
13, 17, 23, 27: Tubes
14, 16, 24, 26: Pumps
15, 25: Reservoirs
15$d$: Drug port
19: Double coaxial balloon catheter
19$c$: Micro balloon
19$p$: Parent balloon
29: Cannula
30: Controller
31: Control section
32: Transmitting-receiving section
33: Memory section
34: Operation section
35: Display section
36: Printer
39: Blood flow meter
42: Embolic coil

The invention claimed is:

1. A pancreas perfusion apparatus for administering a drug topically to a pancreas by percutaneous isolated pancreas perfusion, wherein the drug is a gene therapeutic drug used for a gene therapy, the pancreas perfusion apparatus comprising:
a first vein occlusion section which occludes a first main vein through which a venous blood from the pancreas flows;
a second vein occlusion section which occludes a second vein into which a venous blood from collateral pathways outside the pancreas flows, the second vein being located upstream of the first main vein;
an artery occlusion section which occludes sites where an artery that nourishes the pancreas is connected to arteries that nourish tissues other than the pancreas, the sites being located upstream and downstream of the artery that nourishes the pancreas;
a drug administration section which, in a state that an occlusion area that isolates from other tissues the pancreas as well as arteries and veins performing a blood supply and discharge to/from the pancreas is formed by the each occlusion section, recovers a liquid upstream of said first vein occlusion section and supplies the recovered liquid to the artery that nourishes the pancreas, the upstream and downstream of which are occluded by the artery occlusion section, by using a drug administration pump;

a systemic circulation section which, in a state that the occlusion area is formed, recovers a liquid upstream of said second vein occlusion section and feeds the recovered liquid into a systemic circulation different from the occlusion area by using a systemic circulation pump; and a control device which controls the systemic circulation pump so as to recover the liquid upstream of said second vein occlusion section at a predetermined flow rate, wherein:

said control device comprises:

an administration signal input section for receiving an administration signal indicating that the drug is administered to the drug administration section;

a drug perfusion stopping section for stopping the driving of the drug administration pump at a time point when a first time passes from a time of receiving the administration signal, the administration signal being received during the driving of said drug administration pump and the systemic circulation pump; and a notification section for notifying an end time of the percutaneous isolated pancreas perfusion at a time point when a second time passes after the driving of the drug administration pump is stopped.

2. The pancreas perfusion apparatus according to claim 1, wherein the predetermined flow rate is 150 ml/min. or more.

3. The pancreas perfusion apparatus according to claim 1, wherein:

the first vein is a portal vein and said first vein occlusion section is arranged in a main portal vein in the vicinity of a merging portion of a splenic vein and a superior mesenteric vein;

the second vein is the superior mesenteric vein; and the artery occlusion section comprises:

a first artery occlusion section which occludes a common hepatic artery located upstream of a branching portion of a proper hepatic artery and a gastroduodenal artery;

a second artery occlusion section which occludes a main celiac artery located upstream of a branching portion of the common hepatic artery, a left gastric artery, and a splenic artery; and occlusion sections which occlude the left gastric artery and the splenic artery each at a distal portion farther than a branching portion of the artery nourishing the pancreas.

4. The pancreas perfusion apparatus according to claim 3, wherein the artery occlusion section further comprises a dorsal pancreatic artery occlusion section which occludes a dorsal pancreatic artery branched from a superior mesenteric artery.

5. The pancreas perfusion apparatus according to claim 1, wherein said control device controls the systemic circulation pump so as to recover the liquid upstream of said second vein occlusion section at a flow rate of 300 ml/min. or more when a body weight of a patient is 50 kg or more.

6. The pancreas perfusion apparatus according to claim 1, wherein the first time is a time required for the gene therapeutic drug to reach all the regions of the pancreas and the second time is 15 minutes or more.

7. The pancreas perfusion apparatus according to claim 1, wherein said control device controls the drug administration pump so that a flow rate of the liquid recovered from the upstream side of said first vein occlusion section is higher than that of the liquid supplied to the artery by 0 to 15 ml/min.

8. A method for controlling a pancreas perfusion apparatus for administering a drug topically to a pancreas by percutaneous isolated pancreas perfusion, the pancreas perfusion apparatus comprising:

a first vein occlusion section which occludes a first main vein through which a venous blood from the pancreas flows;

a second vein occlusion section which occludes a second vein into which a venous blood from collateral pathways outside the pancreas flows, said second vein being located upstream of the first main vein;

an artery occlusion section which occludes sites where an artery that nourishes the pancreas is connected to arteries that nourish tissues other than the pancreas, the sites being located upstream and downstream of the artery that nourishes the pancreas;

a drug administration section which, in a state that an occlusion area that isolates from other tissues the pancreas as well as arteries and veins performing a blood supply and discharge to/from the pancreas is formed by the each occlusion section, recovers a liquid upstream of said first vein occlusion section and supplies the recovered liquid to the artery that nourishes the pancreas, the upstream and downstream of which are occluded by the artery occlusion section, by using a drug administration pump;

a systemic circulation section which, in a state that the occlusion area is formed, recovers a liquid upstream of said second vein occlusion section and feeds the recovered liquid into a systemic circulation different from the occlusion area by using a systemic circulation pump; and a control device which controls the systemic circulation pump, wherein the drug is a gene therapeutic drug used for a gene therapy;

said control device comprises an administration signal input section for receiving an administration signal indicating that the drug is administered to the drug administration section;

said control device controls the systemic circulation pump to recover the liquid upstream of said second vein occlusion section at a predetermined flow rate; and said control device carries out:

stopping the driving of the drug administration pump at a time point when a first time passes from a time of receiving the administration signal, the administration signal being received during the driving of the drug administration pump and the systemic circulation pump; and notifying an end time of the percutaneous isolated pancreas perfusion at a time point when a second time passes after the driving of the drug administration pump is stopped.

9. A method for pancreas perfusion for performing a treatment of pancreatic diseases by administering a drug topically to a pancreas of a patient by percutaneous isolated pancreas perfusion, wherein the drug is a gene therapeutic drug used for a gene therapy, the method comprising:

forming an occlusion area that isolates from other tissues the pancreas as well as arteries and veins performing a blood supply and discharge to/from the pancreas by:

occluding a first main vein through which a venous blood from the pancreas flows using a first vein occlusion section;

occluding a second vein into which a venous blood from collateral pathways outside the pancreas flows using a second vein occlusion section, the second vein being located upstream of the first main vein; and occluding sites where an artery that nourishes the pancreas is connected to arteries that nourish tissues other than the pancreas using an artery occlusion section, the sites being located upstream and downstream of the artery that nourishes the pancreas; and performing drug administration/systemic circulation for:

recovering a liquid upstream of said first vein occlusion section and supplying the recovered liquid to the artery that nourishes the pancreas, the upstream and downstream of which are occluded by the artery occlusion section, by using a drug administration pump; and recovering a liquid upstream of said second vein occlusion section at a predetermined flow rate and feeding the recovered liquid into a systemic circulation different from the occlusion area by using a systemic circulation pump, wherein:

the performing of the drug administration/systemic circulation comprises:

performing simultaneous perfusion for a supply of the liquid upstream of said first vein occlusion section to the artery that nourishes the pancreas and a feed of the liquid upstream of said second vein occlusion section to the systemic circulation in the same time by driving the drug administration pump and the systemic circulation pump;

stopping the driving of the drug administration pump at a time point when a first time passes after the simultaneous perfusion is started; and performing the feed of the liquid upstream of said second vein occlusion section to the systemic circulation until a second time passes after the driving of said drug administration pump is stopped.

10. The method for pancreas perfusion according to claim 9, wherein the predetermined flow rate is 150 ml/min. or more.

11. The method for pancreas perfusion according to claim 9, wherein:

the first vein is a portal vein;

the second vein is the superior mesenteric vein;

the artery occlusion section comprises a first artery occlusion section, a second artery occlusion section, and occlusion sections; and, in the forming of the occlusion area:

the first main vein is occluded by arranging said first vein occlusion section in a main portal vein in the vicinity of a merging portion of a splenic vein and a superior mesenteric vein; and the artery that nourishes the pancreas is occluded at sites connected to arteries that nourish tissues other than the pancreas: by occluding a common hepatic artery located upstream of a branching portion of a proper hepatic artery and a gastroduodenal artery by the first artery occlusion section; by occluding a main celiac artery located upstream of a branching portion of the common hepatic artery, a left gastric artery, and a splenic artery by the second artery occlusion section; and by occluding the left gastric artery and the splenic artery each at a distal portion farther than a branching portion of the artery that nourishes the pancreas by the occlusion sections.

12. The method for pancreas perfusion according to claim 11, wherein:

the artery occlusion section further comprises a dorsal pancreatic artery occlusion section; and, in the forming of the occlusion area, the artery that nourishes the pancreas is occluded at the sites connected to the arteries that nourish tissues other than the pancreas further by occluding a dorsal pancreatic artery branched from a superior mesenteric artery by the dorsal pancreatic artery occlusion section.

13. The method for pancreas perfusion according to claim 9, wherein the predetermined flow rate is 300 ml/min. or more when a body weight of the patient is 50 kg or more.

14. The method for pancreas perfusion according to claim 9, wherein the first time is a time required for the gene therapeutic drug to reach all the regions of the pancreas and the second time is 15 minutes or more.

15. The method for pancreas perfusion according to claim 9, wherein, in the performing of the drug administration/systemic circulation, the liquid at the upstream side of said first vein occlusion section is recovered at a flow rate higher than that of the liquid supplied to the artery by 0 to 15 ml/min.

* * * * *